United States Patent [19]

Palm

[11] 4,024,250

[45] May 17, 1977

[54] USE OF DIETARY FRUCTOSE IN THE CONTROL OF HUMAN STRESS RESPONSE

[76] Inventor: J. Daniel Palm, 117 Nevada St., Northfield, Minn. 55057

[22] Filed: Sept. 10, 1975

[21] Appl. No.: 612,031

Related U.S. Application Data

[63] Continuation-in-part of Ser. No. 392,316, Aug. 28, 1973.

[52] U.S. Cl. .................................. 424/180; 536/1
[51] Int. Cl.$^2$ ...................................... A61K 31/70
[58] Field of Search ................................... 424/180

[56] References Cited

OTHER PUBLICATIONS

Schwartz et al., Chem. Abst., vol. 66, 1967 74045c.
MacDonald et al., Chem. Abst. vol. 69, 1968, 1187c.

Primary Examiner—Lewis Gotts
Assistant Examiner—Cary Owens
Attorney, Agent, or Firm—Roy E. Hofer

[57] ABSTRACT

Alleviation of physiologically-induced stress in the human body is provided through a dietary regimen including restriction of carbohydrate intake and administration of substantially pure fructose.

7 Claims, No Drawings

USE OF DIETARY FRUCTOSE IN THE CONTROL OF HUMAN STRESS RESPONSE

This application is a Continuation-in-Part application of previously filed application Ser. No. 392,316, filed Aug. 28, 1973 for a CONTROL OF CHRONIC HYPOGLYCEMIA WITH FRUCTOSE.

BACKGROUND OF THE INVENTION

This invention relates generally to dietary supplement compositions and, more specifically, to the dietary control of physiologically-induced stress by means of oral administration of fructose.

Sugar is the fuel from which body cells obtain energy for cellular activities. When the diet contains carbohydrates, fats and proteins, these foods are broken down to smaller units; sugars, colloidal fats, and short chains of amino acids or individual amino acids by the enzymes and acids of the digestive tract. These smaller molecules are then carried by the blood to the cells which use the sugars immediately or store the excess sugar as glycogen (or fat). The fats are used for various syntheses or are stored for later use while new proteins are made from the amino acids. If no sugars are being added to the blood from the digestive tract the glycogen storage cells, particularly in the liver, convert their stored glycogen into the sugar, glucose. This glucose passes into the blood stream to all of the parts of the body. Normally, the body regulates this concentration of blood glucose within narrow limits. This regulation is controlled by hormones from the endocrine glands.

A short time after the ingestion of carbohydrates a high concentration of simple sugars is present in the blood. The hypothalamic brain cells detect this condition and initiate a set of biochemical readjustments; i.e., they cease their direct and indirect (pituitary pathway) stimulation of the glycogen-converting sympathetic system cells. The pancreas releases insulin into the blood when glucose is present.

Insulin aids the storage of excess sugar by influencing the transport of glucose from the blood stream into the storage cells where it is converted into glycogen. Glycogen is biologically inert and can be reconverted to glucose by an enzyme in the cells. Each molecule of insulin released from the pancreas helps to move thousands of glucose molecules from the blood into the cells before the insulin becomes inactivated by enzymes in the cells.

When a low blood glucose condition exists, the body recognizes this condition as a stress and initiates the stress response; that is, the hypothalamic cells in the brain signal the pituitary to stimulate the adrenal glands to mobilize adrenalin. The pituitary accomplishes this effect by releasing the hormone ACTH (adrenocorticotropic hormone). This hormone stimulates the cells of the outer portion of the adrenal gland to release a hormone called hydroxycortisone. The presence of hydroxycortisone in the blood flowing through the middle or medulla of the adrenal gland causes these cells to release adrenalin. Adrenalin increases the conversion of glycogen to glucose, thereby raising the blood sugar concentration.

The disorder of cell fuel regulation in which the concentration of sugar in the blood stream is so low that the cells are almost starved is called "hypoglycemia." This is not a distinct disease having only one cause, but rather, a stress condition that can be effected by different defects or malfunctions within the regulatory systems of the body. Hypoglycemia becomes a noticeably serious health problem only when the condition is maintained for long periods (chronic hypoglycemia) or when a drastic shift occurs to very low blood sugar levels (acute hypoglycemia). In a mild condition it causes fatigue, nervousness, irritability and insomnia. Hypoglycemia is also associated with obesity, alcoholism, headaches, ulcers and some phychotic disorders.

Problems related to the regulation of blood sugar level and, particularly, low blood sugar are not restricted to any single age group. Rather, it is believed that such varied disorders as colic in babies, hyperactivity in children, ulcers in adults, and certain psychiatric disorders have characteristics which implicate or are associated with difficulties in the regulation of the blood sugar concentration.

When the adrenal gland and steriod-adrenalin-release systems of the body are insufficient or ineffective the blood sugar level will remain low. Fatigue and emotional depression are common features of this type of hypoglycemia. When the body's regulatory systems which convert glucose to glycogen are defective there will be no storage of glycogen. In such a situation, despite large amounts of adrenalin circulating in the blood stream, the blood sugar level will remain low. The excessive amounts of adrenalin can result in hunger pangs, increased tension and anxiety, and can also result in severe headaches. It is further believed that a deficiency of blood sugar and an excess of adrenalin may cause, in some persons, mental confusion, depression and abnormal social behavior.

It should be emphasized, however, that low blood sugar does not have to reach disease proportions in order to be considered a stress. Every time blood sugar drops below a certain threshold level, the stress response will be initiated. Even in a normal individual on a normal diet, such a reaction will occur many times during an average day. In fact, it has been demonstrated that one fourth or more of the total stress response experienced by a normal individual in an average day can be due to blood sugar control.

So, although hypoglycemia creates a more obvious stress with more obvious stress-related symptoms, a "normal" individual can experience a great deal of physiological stress, most or all of which may go completely unrecognized. Since it is generally accepted that stress contributes to such varied disorders as coronary thrombosis, hypertension, peptic ulcers and gallstones in addition to a variety of nervous disorders, this unrecognized physiological stress can be extremely significant.

Chronic hypoglycemia, as discussed herein, is meant to include all of the variants of the low blood sugar condition which are of a generally regular or continual character. When because of an error in the way the body handles the metabolism of sugar, blood glucose levels are constantly below normal, a person is considered to be a "chronic" hypoglycemic. This creates a continuing stress condition and can be manifested by symptoms such as periodic fatigue, anxiety, headaches, food and alcohol cravings, and nervous disorders, etc. which occur over extended periods; i.e., for weeks, months, years and even an entire lifetime. Chronic, or functional, hypoglycemia can be distinguished from acute hypoglycemia in that the latter is essentially a specific instance of a low blood sugar condition which is not of extended duration.

It is believed that one cause of chronic hypoglycemia is that insulin is released by the pancreas into the blood stream so effectively that the glucose which is normally needed for cellular fuel is instead removed from the blood and stored. The body responds to this situation by exercising the control system for increasing blood glucose levels; that is, adrenalin is produced. Because blood levels of glucose are constantly low in a hypoglycemic, adrenalin is almost constantly produced. Normally, adrenalin is also released as a result of other kinds of stress (e.g., environmentally-induced stress), making one alert, on edge and tense. Usually this stress response is transitory and, when the stress is removed, the adrenalin levels decrease and a tranquil condition returns. Chronic hypoglycemia, however, creates in the body a constant stress requiring continual stress response. Depending upon the way a person reacts to the chronic stress situation, and his ability to deal with it, different conditions can result.

As mentioned earlier, one of the consequences of elevated adrenalin in the body is the reaction we normally experience as hunger pangs. A person with chronic hypoglycemia may thus attempt to alleviate the situation by excessive eating. Yet, because of the metabolic error that created the hypoglycemic condition, few of these calories become available to maintain the blood sugar level. They are instead diverted into the production of fat, causing the person a weight-control problem.

If a hypoglycemic person is already a heavy drinker for social and/or emotional reasons, or possibly as a direct result of his physiological stress, he can derive some unexpected physiological benefits from the alcohol. Because alcohol can depress the hypothalamic demand for fuel, the alcoholic can, by taking a drink, experience temporary relief from his stress symptoms. He can experience more permanent relief by drinking a lot. Thus, although he does not realize it, the alcoholic's dependency can be his way of treating the consequences of his hypoglycemia.

It has been suggested that schizophrenia can occur in hypoglycemic persons who are unable to deal with the physiological consequences of the chronic stress response. In these extreme circumstances, the reaction of the individual to his physiological state can be psychotic behavior. Others may respond to the stress in less extreme ways and develop more common stress-related symptoms such as peptic ulcers or hypertension (high blood pressure).

DESCRIPTION OF THE INVENTION

The present invention relates to the discovery that the stress response in humans may be regulated through dietary control and the use of substantially pure fructose as a dietary supplement.

Fructose, or fruit sugar, is a monosaccharide very similar to glucose in chemical makeup. Like glucose, it can serve as a metabolic fuel in the body with the derivation of energy. In fact, because of the way in which it is assimilated and metabolized, fructose may be considered a better energy source than glucose. Of particular importance in the problems of hypoglycemia is the fact that fructose, in a wide range of concentration, will not normally induce the production of insulin. Thus, it is possible for a hypoglycemic person to achieve and maintain normal blood sugar levels by substituting fructose for the glucose and other carbohydrates in his diet.

While fructose is present in both common table sugar (sucrose) and fruits, intake of these foods will not provide an appropriate treatment for hypoglycemic stress since they also include substantial amounts of glucose which will stimulate the release of insulin. The insulin influences transfer of the blood sugars into storage cells which leads again to the hypoglycemic state.

The present invention is directed particularly toward a method for controlling or limiting physiologically-induced stress through dietary control. It has been discovered that a dietary regimen including a reduction in other carbohydrates, coupled with an increase in the consumption of substantially pure fructose, will provide the body with its necessary cellular fuel without stimulating the production of insulin nor the release of adrenalin into the blood stream. In this manner blood sugar levels may be effectively controlled. The stress symptoms associated with the chronic hypoglycemic condition may thus be substantially avoided.

Digestion of most common carbohydrates (starches and sweets) results in increased blood levels of glucose. In most people this, in turn, stimulates insulin production and the decrease of blood glucose, often to below-normal levels. In normal persons this "rebound" hypoglycemia is transitory and the resultant stress is short-lived. In the hypoglycemic person this stress can be extended and produce serious symptoms. It has been discovered that fructose can be used as a part of a total diet in which it is substituted for all or most of the normal carbohydrates. If fructose is eaten in small quantities throughout the day, and other carbohydrates in the diet eliminated or greatly reduced, an individual can maintain normal blood sugar levels and, thus, eliminate hypoglycemic stress and its associated symptoms. In normal individuals this stress component may comprise at least one quarter of the total stress experienced; in the chronically-hypoglycemic person it may constitute a substantially greater portion of his total stress.

Of course, the severity of the hypoglycemic condition may vary from over a wide range and result in a variety of different physiological or psychological symptoms. The dietary regimen, in turn, will depend on the particular stress condition and its symptoms. Generally, however, fructose should be provided as a dietary supplement in the range of about 10 to 100 grams per day.

For the chronic, severe hypoglycemic who displays psychotic or alcoholic tendencies an appropriate dietary regimen should restrict substantially all carbohydrates and require administration of 100 grams of fructose per day, preferably taken at periodic intervals, i.e., several grams per hour. Fructose has been found to be helpful for persons exhibiting such symptoms. By removing the physiological basis of the stress (the hypoglycemic condition) fructose serves essentially as a tranquilizer in these cases.

For others whose symptoms are of a less severe variety, or others who evidence no overt symptoms but wish to diminish their stress component, lighter fructose dosages and lesser restrictions on carbohydrate intake will provide relief. For example, those who suffer from periodic headaches, i.e., "morning headaches" and hunger pangs may avoid these conditions, surprisingly, through elimination of between meal snacks which are high in sugars and starches and substitution therefor of 5 to 20 grams of fructose. Excessive appetite can be the consequence of chronic hypoglycemia. In normal diets there are no constituents to help curb the craving for food. In fact, in hypoglycemics with a weight control problem, ordinary carbohydrates can intensify their problem. However, fructose, when substituted for other carbohydrates in the diet, in amounts of from 10–100 grams per day, can help eliminate the craving for food and make weight loss considerably more tolerable. Even in persons who have not been diagnosed as hypoglycemic, fructose can be used to help curb the appetite and provide the basis for an effective weight loss program.

In most cases it is preferable that the fructose dietary supplement be administered in periodic dosages throughout the day. This not only makes administration of the fructose more palatable to the individual but it also assures an even and constant input of fructose into the blood stream which insures against release of adrenalin and its attendant effects. For example, an individual taking a daily dosage of 80 grams may ingest 6–10 grams per hour through the day. Likewise, those who suffer from symptoms of hypoglycemia between meals should take proportionate dosages at mid-morning, mid-afternoon and late evening.

The substantially pure fructose dietary supplement of this invention is meant to include all compositions which contain fructose and substantially no other metabolizable carbohydrate. Sucrose and fruits, therefore, although they contain fructose would be unacceptable because of the significant amounts of glucose found therein.

The fructose dietary supplement of this invention may be taken as a tablet or syrup or it may be utilized as a sweetener in drinks and beverages and other foods. In this connection it should be noted that most people find fructose sweeter than common table sugar.

Tablets which have been found to be of convenient oral dosage form for dietary use include about 2 grams of fructose and small amounts of flavoring and coloring additives. These may be particularly effective for those who exhibit cravings for food and drink as symptoms of their physiological stress. During such a stress episode, intake of 3–5 fructose tablets (6 to 10 grams) can help to alleviate these symptoms and fructose can operate in this manner, as a crave-control dietary supplement.

It should be understood that various modifications of the preferred embodiments of this invention as discussed herein can be made without departing from the spirit and the scope of the invention.

I claim:

1. A method for relieving the physiologically-induced stress response in the human body which comprises the steps of restricting the consumption of carbohydrates and substituting for said carbohydrates a substantially pure fructose dietary supplement.

2. The method of claim 1 wherein said fructose dietary supplement is substituted for said carbohydrates in a dosage in the range of about 10 to 100 grams per day.

3. The method of claim 1 wherein said carbohydrate restriction is substantially complete and said fructose dietary supplement is substituted therefor in a dosage in the range of about 10 to 100 grams per day.

4. The method of claim 3 wherein said fructose dietary supplement is administered in proportionate hourly dosages.

5. A method of alleviating the symptoms of physiologically-induced stress which comprises administering to the patient substantially pure fructose in the amount of from about 10 to 100 grams per day, and restricting the patient's consumption of carbohydrates throughout the day.

6. An oral dosage, tablet form for the control of the human stress response comprising substantially pure fructose.

7. The tablet form of claim 7 wherein said fructose is present in an amount of about 2 grams.

* * * * *